(12) United States Patent
Rothfuss et al.

(10) Patent No.: US 10,226,055 B2
(45) Date of Patent: Mar. 12, 2019

(54) PHASE CHANGE SYSTEMS AND METHODS FOR THEIR PREPARATION AND USE

(71) Applicant: EMPIRE TECHNOLOGY DEVELOPMENT LLC, Wilmington, DE (US)

(72) Inventors: Christopher J. Rothfuss, Laramie, WY (US); Bradley Kirk Roberts, Seattle, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 139 days.

(21) Appl. No.: 15/110,699

(22) PCT Filed: Jan. 8, 2014

(86) PCT No.: PCT/US2014/010685
§ 371 (c)(1),
(2) Date: Jul. 8, 2016

(87) PCT Pub. No.: WO2015/105485
PCT Pub. Date: Jul. 16, 2015

(65) Prior Publication Data
US 2016/0324171 A1 Nov. 10, 2016

(51) Int. Cl.
| | | |
|---|---|---|
| *A23B 7/144* | (2006.01) | |
| *A23L 3/3409* | (2006.01) | |
| *G01N 31/22* | (2006.01) | |
| *A61K 8/11* | (2006.01) | |
| *A61K 8/37* | (2006.01) | |
| *A61K 8/60* | (2006.01) | |
| *A61K 8/92* | (2006.01) | |
| *A61Q 19/10* | (2006.01) | |

(52) U.S. Cl.
CPC .......... *A23B 7/144* (2013.01); *A23L 3/34095* (2013.01); *A61K 8/11* (2013.01); *A61K 8/37* (2013.01); *A61K 8/60* (2013.01); *A61K 8/922* (2013.01); *A61Q 19/10* (2013.01); *G01N 31/22* (2013.01); *A23V 2002/00* (2013.01)

(58) Field of Classification Search
CPC ....... A23B 7/144; A23L 3/34095; A61K 8/11; A61K 8/37; A61K 8/60; A61K 8/922; A61Q 19/10; G01N 31/22; A23V 2002/00
See application file for complete search history.

(56) References Cited

U.S. PATENT DOCUMENTS 4,601,588 A 7/1986 Takahara et al.
8,147,760 B1 4/2012 Huvard et al.
2004/0182304 A1 9/2004 Cooperman
2007/0151502 A1 7/2007 Cooperman
2008/0272332 A1 11/2008 Joseph et al.
2009/0105371 A1 4/2009 Luster-Teasley
2011/0195875 A1 8/2011 Swearingen et al.
2012/0138275 A1 6/2012 Biggin et al.
2013/0119301 A1 5/2013 Sunol et al.

FOREIGN PATENT DOCUMENTS

DE 100 59 972 * 11/2002

OTHER PUBLICATIONS

Oils—Melting Points, accessed at https://web.archive.org/web/20131031013251/http://www.engineeringtoolbox.com/oil-melting-points-d_1088.html, accessed on Jun. 24, 2016, pp. 2.
Bayes-Garcia et al., Phase Change Materials (PCM) microcapsules with different shell compositions: Preparation, characterization and thermal stability, Solar Energy Materials and Solar Cells (Jul. 2010), 94(7) pp. 1235-1240.
Binks, Particles as surfactants-similarities and differences, Current Opinion in Colloid & Interface Science (Mar. 2002), 7(1-2) pp. 21-41.
Hagenmaier and Shaw, Gas Permeability of Fruit Coating Waxes, Journal of the American Society for Horticultural Science (Jan. 1992), 117(1) pp. 105-109.
International Search Report and Written Opinion for International Application No. PCT/US2014/010685 dated May 6, 2014.
Johnston et al., Composite nano-structured calcium silicate phase change materials for thermal buffering in food packaging, Current Applied Physics (May 2008), 8(3-4) pp. 508-511.
Medina et al., On the heat transfer rate reduction of structural insulated panels (SIPs) outfitted with phase change materials (PCMs), Energy (Apr. 2008), 33(4) pp. 667-678.
Mondal, Phase change materials for smart textiles—An overview, Applied Thermal Engineering (Aug. 2008), 28 (11-12) pp. 1536-1550.
Nassu and Goncalves, Determination of melting point of vegetable oils and fats by differential scanning calorimetry (DSC) technique, Grasas y Aceites (Jan. 1999), 50(1) pp. 16-21.
Suppes et al., Latent heat characteristics of fatty acid derivatives pursuant phase change material applications, Chemical Engineering Science (May 2003), 58(9) pp. 1751-1763.
Tan and Fok, Cooling of helmet with phase change material, Applied Thermal Engineering (Dec. 2006), 26 pp. 2067-2072.
Zalba, Review on thermal energy storage with phase change: materials, heat transfer analysis and applications, Applied Thermal Engineering (Feb. 2003), 23(3) pp. 251-283.

* cited by examiner

*Primary Examiner* — Irina S Zemel (57) ABSTRACT

A phase change system and methods of making a phase change system are disclosed. A multiple phase change system is also disclosed. The system may include at least one phase change material and at least one chemical reactant encapsulated within the phase change material. The chemical reactant may react with another chemical reactant or the surrounding environment.

8 Claims, 8 Drawing Sheets

PHASE CHANGE SYSTEMS AND METHODS FOR THEIR PREPARATION AND USE

CROSS-REFERENCE TO RELATED APPLICATIONS

This Application is a U.S. National Stage filing under 35 U.S.C. § 371 of International Application No. PCT/US2014/010685, filed on Jan. 8, 2014 entitled "PHASE CHANGE SYSTEMS AND METHODS FOR THEIR PREPARATION AND USE," which is incorporated herein by reference in its entirety.

BACKGROUND

Phase change materials have the ability to store and release heat energy by changing from one physical state to another. Phase change materials can be used for thermal energy storage technologies as the transition from one physical state to another requires a large quantity of heat transfer within a specific temperature range. Technologies such as improved building insulation panels, thermostatic food packaging, and thermoregulating clothing may use phase change materials.

The use of phase change materials beyond thermoregulation technologies could extend the application of phase change materials. New systems incorporating phase change materials to contain and manage chemical systems, and that may be inexpensively produced, would be beneficial.

SUMMARY

The technologies described in this document are not limited to the particular systems, methodologies or protocols described, as these may vary. The terminology used herein is for the purpose of describing particular embodiments only, and is not intended to limit the scope of the present disclosure.

Presently disclosed are methods of making a phase change system. The method may include encapsulating at least one chemical reactant in at least one phase change material. The at least one phase change material may be configured to change from a solid phase to a liquid phase at or above at least one phase transition temperature of the at least one phase change material to release the at least one chemical reactant into the liquid phase of the at least one phase change material. In some embodiments, the encapsulating may include adding a first phase change material in a liquid phase, solidifying the first phase change material, and inserting the at least one chemical reactant into the first phase change material after the solidifying step. Alternatively, the at least one chemical reactant may be added before or during solidification.

In an embodiment, phase change systems may include at least one phase change material in a solid form, and at least one chemical reactant encapsulated within the at least one phase change material. The at least one phase change material may be configured to change from a solid phase to a liquid phase at or above at least one phase transition temperature of the at least one phase change material which may release the at least one chemical reactant into the liquid phase of the at least one phase change material.

In an embodiment, multiple phase change systems may include two or more phase change systems. Each system may include at least one phase change material in solid form and at least one chemical reactant encapsulated within the at least one phase change material. The at least one phase change material in solid form may be configured to change from a solid phase to a liquid phase at or above at least one phase transition temperature of the at least one phase change material to release the at least one chemical reactant into the liquid phase of the at least one phase change material.

In an embodiment, methods of using a phase change system to detect a temperature change may include providing a phase change system and determining the temperature change from the system based on an amount of the at least one chemical reactant released into the at least one phase change material. The phase change system may include at least one phase change material in a solid form and at least one chemical reactant encapsulated within the at least one phase change material.

In an embodiment, methods of using a phase change system to react with at least one target material may include providing a phase change system and detecting a reaction with the at least one target material based on an amount of the at least one chemical reactant reacting with the at least one target material. The phase change system may include at least one phase change material in a solid form and at least one chemical reactant encapsulated within the at least one phase change material.

DETAILED DESCRIPTION

The technologies described in this document are not limited to the particular systems, methodologies or protocols described, as these may vary. The terminology used herein is for the purpose of describing particular embodiments only, and is not intended to limit the scope of the present disclosure.

It must be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. As used herein, the term "comprising" means "including, but not limited to."

The following terms shall have, for the purposes of this application, the respective meanings set forth below.

A "phase change material" refers to any material that changes from one physical state to another and either absorbs or releases heat during the process. Phase change materials can be organic or inorganic, such as paraffins, vegetable oils, inorganic salt mixtures, or other materials as will be described in the disclosed embodiments.

A "chemical reactant" refers to any substance that causes a reaction when the substance interacts with another substance. The substances can produce a useful effect or product as a result of the reaction.

A "discrete unit" refers to any compartment of a system that is separate from another compartment. For example, a discrete unit in a system would contain a chemical reactant that is separated from another discrete unit with a second chemical reactant.

A "getter" material refers to any material that is used to remove impurities. For example, a getter material would absorb traces of gas from a surrounding environment.

Figure 1:
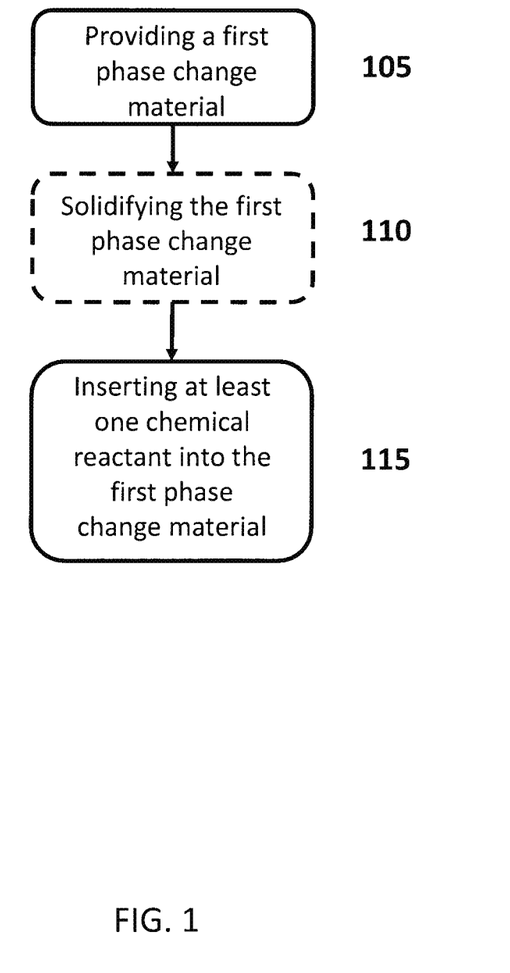
FIG. 1 depicts a flowchart of an illustrative method of making a phase change system according to an embodiment.

FIG. 1 depicts a flowchart of an illustrative method of making a phase change system according to an embodiment. The method may include encapsulating at least one chemical reactant in at least one phase change material. The at least one phase change material may be configured to change from a solid phase to a liquid phase at or above at least one phase transition temperature of the at least one phase change material to release the at least one chemical reactant into the liquid phase of the at least one phase change material.

In some embodiments, the at least one chemical reactant may be a liquid, a liquid dispersed in capsules, a gas, a gas dispersed in capsules, a solid, a solid dispersed in capsules, or a combination thereof. The at least one chemical reactant may be acetic acid, ammonium hydroxide, calcium hydroxide, carbonic acid, fragrant oils, deodorants, hydrochloric acid, hydrogen peroxide, insect pheromones, insect pesticides, magnesium, nitric acid, oxygen gas, palladium, perfume chemicals, platinum, potassium hydroxide, a salt, sodium hydroxide, sulphuric acid, titanium dioxide, zinc oxide, silicon dioxide, a bicarbonate, or a combination thereof. In some embodiments, the at least one chemical reactant may have a fluorescent tag. In some embodiments, the at least one chemical reactant may be chemically inert with respect to the at least one phase change material that encapsulates the at least one chemical reactant. In other embodiments, the at least one chemical reactant may be bioluminescent, chemiluminescent, phosphorescent, or a combination thereof. In further embodiments, the at least one chemical reactant may be a fire-extinguishing compound. In yet further embodiments, the at least one chemical reactant may be electrically conductive.

Examples of fragrant oils may be essential oils or synthetic fragrant oils. Examples of deodorants may be cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, phenoxyethanol, or a combination thereof.

In some embodiments, the at least one chemical reactant may include at least two chemical reactants. The at least two chemical reactants may be capable of reacting with each other when contacted. The at least one chemical reactant may be a plurality of chemical reactants. In some embodiments, the at least one chemical reactant may be in the form of a plurality of microcapsules.

In some embodiments, the at least one phase change material may be a salt hydrate, polyethylene glycol, a wax, a fatty acid compound, or a combination thereof. In other embodiments, the at least one phase change material may be paraffin wax, polyethylene wax, tetrafluoroethylene wax, spermaceti, lanolin, ouricury wax, candelilla wax, epicuticular wax, retamo wax, tallow, or a combination thereof. In further embodiments, the at least one phase change material may be coconut oil, rice oil, soybean oil, cocoa butter, palm stearin, or a combination thereof. The at least one phase change material may be a paraffin wax. In some embodiments, the at least one phase change material may have low gas permeability.

In some embodiments, the at least one phase change material may have a geometric shape. In other embodiments, the at least one phase change material may be formed in a solid phase into a geometric shape. The geometric shape may be a film, a sheet, a cube, a cuboid, a square-based pyramid, a triangular-based pyramid, a triangular prism, a hexagonal prism, a cone, a sphere, a cylinder, a tube, or a combination thereof. The at least one phase change material may be formed by conventional manufacturing techniques. For example, manufacturing techniques may be extrusion, hot drawing, cold drawing, casting, 3D printing, or a combination thereof.

In some embodiments, the at least one phase change material may be a blend of two or more different phase change materials. The at least one phase change material may be a plurality of phase change materials. In some embodiments, the plurality of phase change materials may be arranged in discrete units. The discrete units may be layers, capsules, or other defined spaces. In some embodiments, the discrete units may be in adjacent planar layers. In some embodiments, the plurality of phase change materials may be in adjacent planar layers by order of increasing phase transition temperature. The arrangement by order of increasing phase transition temperature may be used to produce a gradient response, where each layer increases or decreases the intensity of the reaction. The arrangement by order of increasing phase transition temperature may also produce a stepwise series of distinct chemical reactions. In some embodiments, each discrete unit may encapsulate a chemical reactant. The discrete units may encapsulate a plurality of chemical reactants. In some embodiments, at least one chemical reactant in one discrete unit may react with at least one chemical reactant in a second adjacent discrete unit. Each of the plurality of chemical reactants may be individually encapsulated within the at least one phase change material.

The at least one phase change material may act as a barrier when in a solid phase. The barrier separates one reactant from another to prevent the at least one chemical reactant from producing a chemical reaction with another chemical reactant. When the at least one phase change material is in a liquid phase the material may provide a diffusion rate-limited medium for combining the at least one chemical reactant with another chemical reactant. The rate at which the at least one phase change material changes from a solid phase to a liquid phase may depend on the phase transition temperature and latent heat of fusion of the phase change material.

Convection currents within the at least one phase change material in the liquid phase may bring the reactants closer together to eventually combine the chemical reactants to produce a chemical reaction. The rate at which the chemical reactants release from the at least one phase change materials and combine may be dependent upon the fluid properties of the phase change materials, the strength of the convection currents within the at least one phase change material in the liquid phase, and the solubility of the chemical reactants, among other factors. For example, fluid properties may include density, viscosity, surface tension, specific weight, specific gravity, or a combination thereof.

In some embodiments, the at least one phase transition temperature of the at least one phase change material may be generally any temperature, such as about −5° C. to about 200° C. In other embodiments, the phase transition temperature of the at least one phase change material may be about 50° C. to about 100° C. For example, the phase transition temperature of the at least one phase change material may be about −5° C., about 0° C., about 10° C., about 20° C., about 30° C., about 40° C., about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., or a range between any of these values (including endpoints). In some embodiments, the at least one phase transition temperature may be reached when a temperature of an environment surrounding the system is the at least one phase transition temperature, a presence of at least one target material reacts with the chemical reactant, or a combination thereof.

In some embodiments, the at least one phase change material may have a plurality of phase transition temperatures. Each of the phase transition temperatures may be different such that a chemical reactant in one phase change material completely activates at a first phase transition temperature before another phase change material encapsulating a different chemical reactant begins to change from the solid phase to the liquid phase at a second phase transition temperature.

In some embodiments, the at least one chemical reactant may trigger at least one event when released into the liquid phase of the at least one phase change material at or above the at least one phase transition temperature of the at least one phase change material. The at least one event may be an endothermic reaction, an exothermic reaction, a color change, an odor release, combustion, adsorption of a compound, or a combination thereof. In some embodiments, where the event may be an exothermic reaction, examples may include an improved portable warmer or an improved thermostatic food packaging. In some embodiments, where the event may be an endothermic reaction, examples may include an improved cold pack or an improved thermostatic food packaging.

In some embodiments, the release of the at least one chemical reactant into the liquid phase of the at least one phase change material may produce at least one byproduct. The byproduct may be heat, an oxygen scavenger, a sanitization agent, a corrosive compound, an electrically conductive compound, an insulative compound, a chemical dye, a pigment, a ripening agent, a curing agent, a colloidal compound, or a combination thereof. In other embodiments, the at least one chemical reactant in one discrete unit may react with the at least one byproduct of at least one chemical reactant in a second adjacent discrete unit. In some embodiments, the at least one phase change material, the at least one chemical reactant, and the byproduct may be food-grade substances to be used with food products. For example, food products may be vegetables, fruits, dairy products, breads, cereals, meats, fish, poultry, nuts, seeds, or a combination thereof.

In some embodiments, when the byproduct is a sanitization agent, the sanitization agent may protect consumable resources. The protection of consumable resources may be, for example, the creation or release of encapsulated antibiotic, antimicrobial, or purification agents. In some embodiments, when the byproduct is a corrosive compound, the corrosive compound may be used to target failure of materials. In other embodiments, the byproduct may be used to target reinforcement of materials. In some embodiments, when the byproduct is an oxygen scavenger, the oxygen scavenger may be a getter material or an encapsulated vacuum.

In some embodiments, the at least one chemical reactant reacts with at least one target material. The target material may be a chemical reactant. In some embodiments, the at least one target material may be a plurality of target materials. The target material may be water, a solvent, a pesticide, a hormone, a microorganism, a dye composition, a polymer, hydrogen gas, an acid, a base, a volatile organic compound, or a combination thereof. In some embodiments, the at least one chemical reactant may produce a byproduct when reacted with at least one target material.

As shown in FIG. 1, a first phase change material may be provided 105. The first phase change material may be in a liquid phase. The first phase change material may be added into a container. The container may be an empty container or any container that has available space to accommodate the phase change material. The container may be of a particular shape or volume, such as a cube, a cuboid, a square-based pyramid, a triangular-based pyramid, a triangular prism, a hexagonal prism, a cone, a sphere, a cylinder, or a combination thereof. The first phase change material may be added 105 to the container by any means known in the art. For example, the material may be added by pouring the material, adding the material dropwise, dispensing the material, or the like.

Optionally, in some embodiments, the first phase change material may be solidified 110. The first phase change material may be a solid to a liquid phase change material. In the solid phase, the first phase change material may encapsulate the at least one chemical reactant. The solidified first phase change material may prevent the at least one chemical reactant from interacting with any other reactant, material, or target material. The solidified first phase change material may also prevent the at least one chemical reactant from reacting with the ambient atmosphere.

At least one chemical reactant may be inserted 115 into the first phase change material. In some embodiments, inserting 115 the at least one chemical reactant into the first phase change material may occur after the solidifying 110 step. In other embodiments, inserting 115 the at least one chemical reactant into the first phase change material may occur before the solidifying step. The at least one chemical reactant may be inserted 115 at any general location inside the first phase change material.

The at least one chemical reactant may be inserted 115 into the first phase change material using any generally known method in the art. For example, the at least one chemical reactant may be inserted 115 into the first phase change material by injection of liquid reactants into the first phase change material after it has solidified 110; encapsulating the reactants and dispersing the capsules containing reactants in the liquid form of the first phase change material; encapsulating the reactants, distributing the capsules containing reactants across a layer of the first phase change material, and then layering additional first phase change material on top of the capsules containing reactants; pouring liquid reactants into pre-formed cavities in the solid first phase change material; or bubbling gaseous reactants through the liquid form of the first phase change material and solidifying 110 the first phase change material.

In some embodiments, at least one second phase change material in a liquid phase may be applied on at least a portion of the first phase change material and the at least one chemical reactant. The at least one second phase change material may be solidified after applying the at least one second phase change material. In some embodiments, the at least one second phase change material may be a salt hydrate, polyethylene glycol, a wax, a fatty acid compound, or a combination thereof. In other embodiments, the at least one second phase change material may be paraffin wax, polyethylene wax, tetrafluoroethylene wax, spermaceti, lanolin, ouricury wax, candelilla wax, epicuticular wax, retamo wax, tallow, or a combination thereof. In further embodiments, the at least one second phase change material may be coconut oil, rice oil, soybean oil, cocoa butter, palm stearin, or a combination thereof. The at least one second phase change material may be a paraffin wax.

In some embodiments, the at least one second phase change material may be formed in a solid phase into a geometric shape. The geometric shape may generally be any shape, such as a film, a sheet, a cube, a cuboid, a square-based pyramid, a triangular-based pyramid, a triangular prism, a hexagonal prism, a cone, a sphere, a cylinder, a tube, or a combination thereof.

In some embodiments, the at least one second phase change material may be a blend of two or more different phase change materials. The at least one second phase change material may be a plurality of phase change materials.

In some embodiments, the at least one phase transition temperature of the at least one second phase change material may be generally any temperature, such as about −5° C. to about 200° C. In other embodiments, the phase transition temperature of the at least one second phase change material may be about 50° C. to about 100° C. For example, the phase transition temperature of the at least one second phase change material may be about −5° C., about 0° C., about 10° C., about 20° C., about 30° C., about 40° C., about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., or a range between any of these values (including endpoints). In some embodiments, the at least one second phase change material may have a plurality of phase transition temperatures.

In some embodiments, a coating may be applied over at least a portion of the first phase change material and the at least one chemical reactant. In other embodiments, a coating may be applied over at least a portion of the first phase change material, the at least one chemical reactant, and at least a portion of the second phase change material. The coating may be a semi-permeable membrane. The coating may be a polymer, a sugar, a wax, a paper, a fabric, a foil, a foam, a gel, a membrane, an intercalated system, a fractal surface, or a combination thereof.

Figure 2:
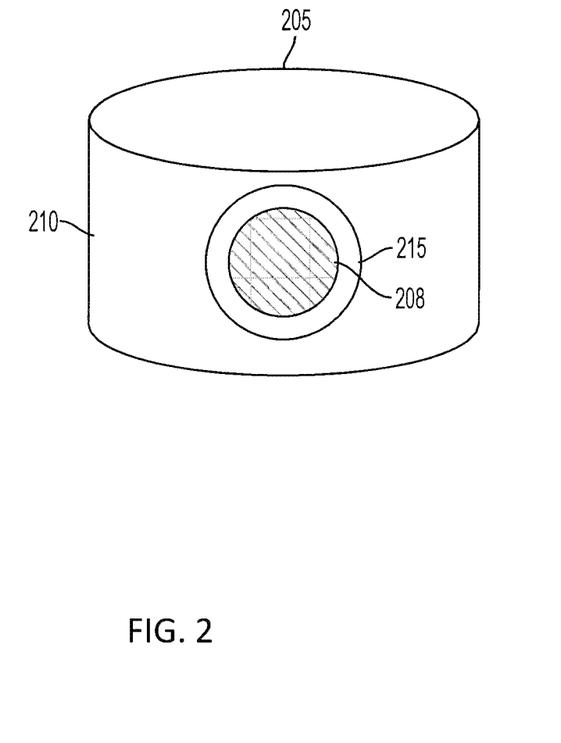
FIG. 2 depicts an illustration of a phase change system according to an embodiment.

FIG. 2 depicts an illustration of a phase change system 205 according to an embodiment. In some embodiments, the phase change system 205 may include at least one phase change material 210 and at least one chemical reactant 208. The chemical reactant 208 may be encapsulated within the at least one phase change material 210. In some embodiments, the phase change system 205 may have a reservoir 215 for the at least one chemical reactant 208. The reservoir 215 may be positioned within the at least one phase change material.

The reservoir 215 may be of any generally known regular shape, irregular shape, or geometric shape. For example, the reservoir 215 may be a cube, a cuboid, a square-based pyramid, a triangular-based pyramid, a triangular prism, a hexagonal prism, a cone, a sphere, a cylinder, a tube, or a combination thereof. In some embodiments, the reservoir 215 may be of any irregular geometric shape.

In some embodiments, the at least one phase change material 210 may be configured to change from a solid phase to a liquid phase at or above at least one phase transition temperature of the at least one phase change material 210 to release the at least one chemical reactant 208 into the liquid phase of the at least one phase change material 210. In some embodiments, the at least one phase change material 210 may be configured to release the at least one chemical reactant 208 at a set time. For example, the at least one phase change material 210 may have a selected shape and selected composition that at exposure to the phase transition temperature will release the encapsulated at least one chemical reactant 208 after a set time.

The phase change system 205 may have a coating over at least a portion of the phase change material 210 and the at least one chemical reactant 208. The coating may be a semi-permeable membrane. The coating may be a polymer, a sugar, a wax, a paper, a fabric, a foil, a foam, a gel, a membrane, an intercalated system, a fractal surface, or a combination thereof.

In some embodiments, the phase change system 205 may be programmable to trigger at least one event. The phase change system 205 may be programmable to trigger a plurality of events.

In some embodiments, the phase change system 205 may be used to detect a temperature change by providing a phase change system 205 and determining a temperature change from the system 205 based on an amount of the at least one chemical reactant 208 released into the at least one phase change material 210. The phase change system 205 may have at least one phase change material 210 in a solid form and at least one chemical reactant 208 encapsulated within the at least one phase change material 210.

In other embodiments, the phase change system 205 may be used to react with at least one target material by providing a phase change system 205 and detecting a reaction with the at least one target material based on an amount of the at least one chemical reactant 208 reacting with the at least one target material. The phase change system 205 may have at least one phase change material 210 in a solid form and at least one chemical reactant 208 encapsulated within the at least one phase change material 210.

Figure 3:
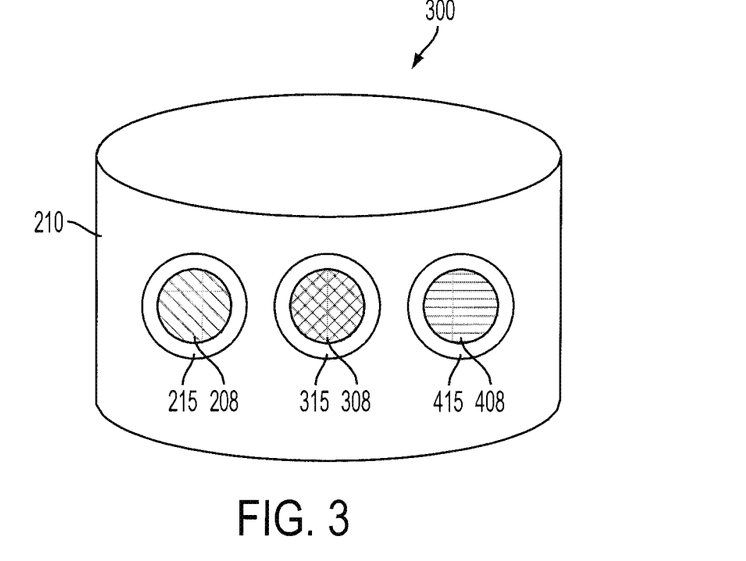
FIG. 3 depicts an illustration of a phase change system with multiple chemical reactants according to an embodiment.

FIG. 3 depicts an illustration of a phase change system 300 with multiple chemical reactants 208, 308, 408 according to an embodiment. The phase change system 300 may have at least one phase change material 210 in a solid form and may have multiple chemical reactants 208, 308, 408. The multiple chemical reactants 208, 308, 408 may be encapsulated within the at least one phase change material 210. The phase change system 300 may have a separate reservoir 215, 315, 415 for each chemical reactant 208, 308, 408, respectively. The multiple reservoirs 215, 315, 415 may be positioned within the at least one phase change material.

As shown in FIG. 3, the phase change system 300 uses one phase change material 210 and three chemical reactants 208, 308, 408 in three separate reservoirs 215, 315, 415, respectively. These chemical reactants 208, 308, 408 may be the same or complementary to yield a desired reaction. In some embodiments, upon reaching the transition temperature for the phase change material 210, the phase change material 210 transitions to a liquid, freeing the chemical reactants 208, 308, 408 to react with one another. In other embodiments, upon reaching the transition temperature for the phase change material 210, the phase change material 210 transitions to a liquid, freeing the chemical reactants 208, 308, 408 to react with at least one target material. In some embodiments, additional phase change materials may be used, including separate distinct units, for example layers or beads, where each distinct unit incorporates one or more chemical reactant.

Figure 4:
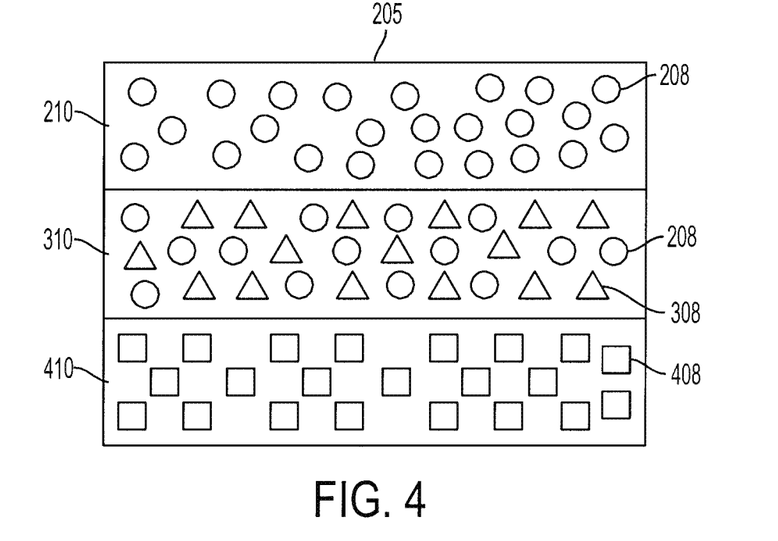
FIG. 4 depicts an illustration of a phase change system with stacked layers according to an embodiment.

FIG. 4 depicts an illustration of a phase change system 205 where the phase change materials 210, 310, 410 are stacked in layers with multiple encapsulated chemical reactants 208, 308, 408 according to an embodiment. The phase change system 205 uses three phase change materials 210, 310, 410. The first phase change material 210 has a first encapsulated chemical reactant 208. The second phase change material 310 has a first and second encapsulated chemical reactant 208, 308. The third phase change material 410 has a third encapsulated chemical reactant 408. Each phase change material 210, 310, 410 has a different phase transition temperature. The first phase change material 210 has a first phase transition temperature. The second phase change material 310 has a second phase transition temperature. The third phase change material 410 has a third phase transition temperature. In some embodiments, the first phase transition temperature is lower than the second phase transition temperature, and the second phase transition temperature is lower temperature than the third phase transition temperature. The first phase change material 210 melts first after reaching the first phase transition temperature, and releases the first chemical reactant 208. Upon reaching the second phase transition temperature, the second phase change material 308 releases the first and second chemical reactants 208, 308. Upon reaching the third phase transition temperature, the third phase change material 410 melts and releases the third chemical reactant 408. In some embodiments, the chemical reactants 208, 308, 408 may be released and may react with at least one target material. In other embodiments, the chemical reactants 208, 308, 408 may be released and interact with one another. In further embodiments, each chemical reactant 208, 308, 408 may produce a byproduct.

Figure 5:
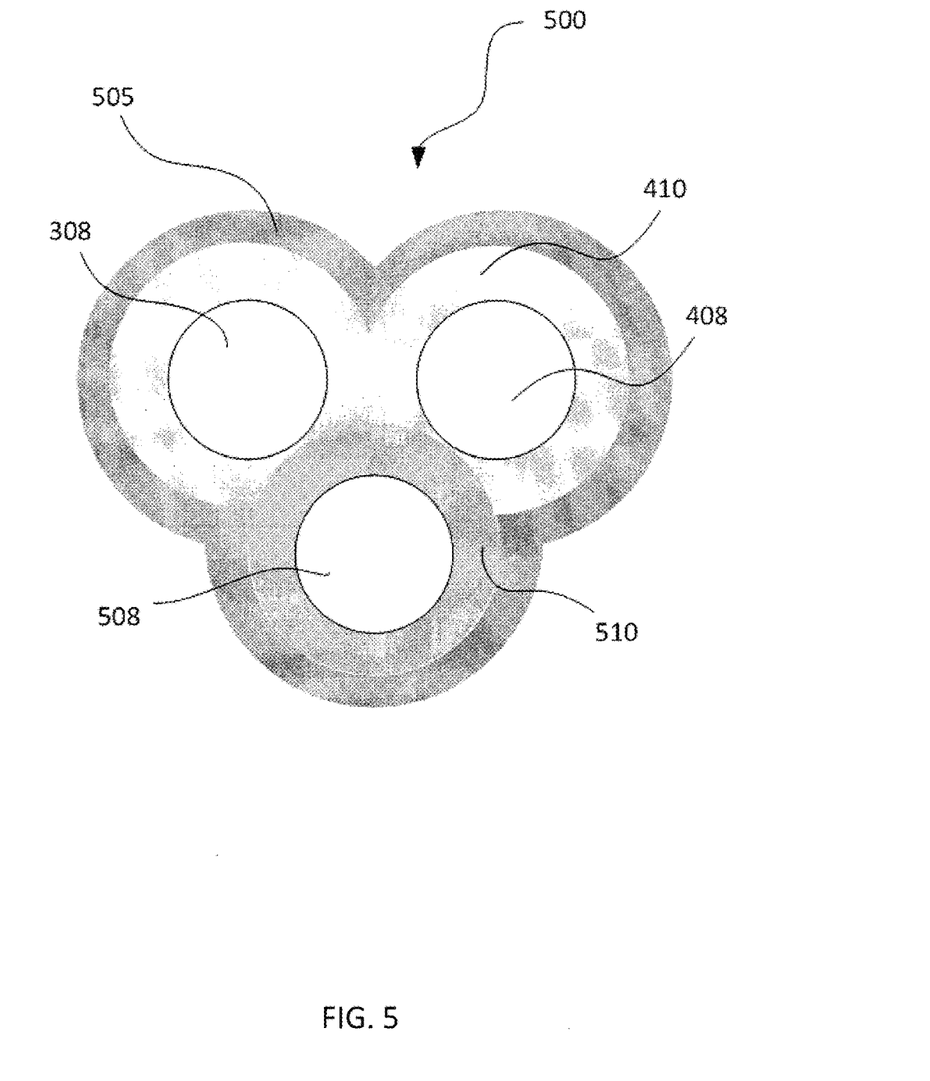
FIG. 5 depicts an illustration of a multiple phase change system according to an embodiment.

FIG. 5 depicts an illustration of a multiple phase change system 500 according to an embodiment. The multiple phase change system 500 may have two or more phase change systems. In some embodiments, the multiple phase change system 500 may include at least one phase change material 410, 510 and at least one chemical reactant 308, 408, 508. The at least one chemical reactant 308, 408, 508 may be encapsulated within the at least one phase change material 410, 510. As will be appreciated from FIG. 5, this type of system is readily adapted to the use of multiple beads of various phase change materials encapsulating one or more desired reactants.

In some embodiments, the multiple phase change system 300 may have a reservoir for each chemical reactant 308, 408, 508. The reservoir may be positioned within each of the phase change materials 410, 510. The reservoir may be of any generally known geometric shape. For example, the reservoir may be a cube, a cuboid, a square-based pyramid, a triangular-based pyramid, a triangular prism, a hexagonal prism, a cone, a sphere, a cylinder, a tube, or a combination thereof.

In some embodiments, the at least one phase change material 410, 510 may be configured to change from a solid phase to a liquid phase at or above at least one phase transition temperature of the at least one phase change material 410, 510 to release the at least one chemical reactant 308, 408, 508 into the liquid phase of the at least one phase change material 410, 510. In some embodiments, the at least one chemical reactant 308, 408, 508 may react with at least one phase change material 410, 510 that is not encapsulating the at least one chemical reactant 308, 408, 508. For example, the at least one chemical reactant 308 may react with the at least one phase change material 510.

As shown in FIG. 5, the multiple phase change system 500 uses two different phase change materials 410, 510. Phase change material 410 encapsulates two chemical reactants 308, 408. These chemical reactants 308, 408 may be the same or complementary to yield a desired reaction. Upon reaching the transition temperature for phase change material 410, the phase change material 410 transitions to a liquid, freeing the two chemical reactants 308, 408 to react with one another. This reaction may give off heat causing the second phase change material 510 to transition to a liquid. This transition frees a third chemical reactant 508 to react with the first two chemical reactants 308, 408, or the products thereof. In some embodiments, the third chemical reactant 508 acts to quench the first reaction.

The multiple phase change system 500 may have a coating 505 over at least a portion of the system 500. The coating 505 may be a semi-permeable membrane. The coating 505 may be a polymer, a sugar, a wax, a paper, a fabric, a foil, a foam, a gel, a membrane, an intercalated system, a fractal surface, or a combination thereof.

In some embodiments, each of the two or more systems in the multiple phase change system 500 may be in the form of a layer. The layers may be arranged by order of increasing phase transition temperatures. In other embodiments, each of the two or more systems in the multiple phase change system 500 may be in the form of a capsule. The capsules may be arranged in a three-dimensional configuration by order of increasing phase transition temperatures. The arrangement by order of increasing phase transition temperature may be used to produce a gradient response, where each layer or capsule increases or decreases the intensity of the reaction. The arrangement by order of increasing phase transition temperature may also produce a stepwise series of distinct chemical reactions. Each capsule may contain a separate chemical reactant.

In some embodiments, the multiple phase change system 500 may be programmable to trigger at least one event. In other embodiments, each system 500 may trigger one event. In some embodiments, each system 500 may trigger a separate event.

EXAMPLES

Example 1: A Phase Change System for a Storage Device for Chemicals

Figure 6:
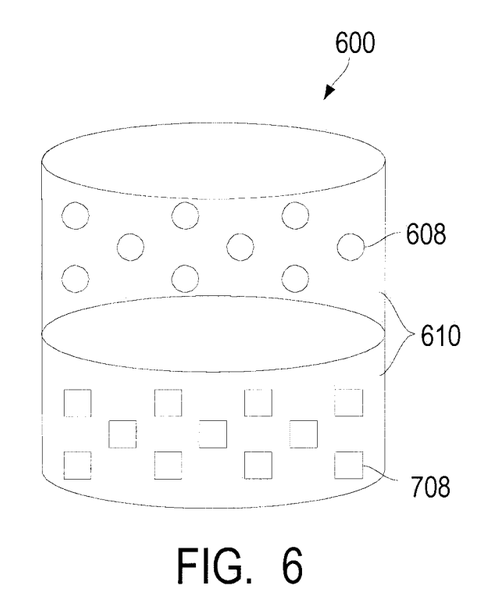
FIG. 6 depicts a storage device for chemicals.

A phase change system will be made to contain two chemical reactants, which upon release from a phase change material will cause a chemical reaction. FIG. 6 shows an illustration of such a system 600. A system 600 will have solidified cocoa butter as the phase change material 610, and will have two distinct cylindrical layers. Each cylindrical layer of cocoa butter 610 will be 2 centimeters thick and have a diameter of 10 centimeters. The first layer will encapsulate bicarbonate 608 and the second layer will encapsulate acetic acid 708. The system 600 will be removed from a cool storage location and allowed to melt. As the cocoa butter 610 melts, the acetic acid 708 and bicarbonate 608 will mix and react causing a reaction that produces carbon dioxide and water. Such a reaction could be used to create a protective carbon dioxide blanket within a storage device for chemicals.

Figure 7:
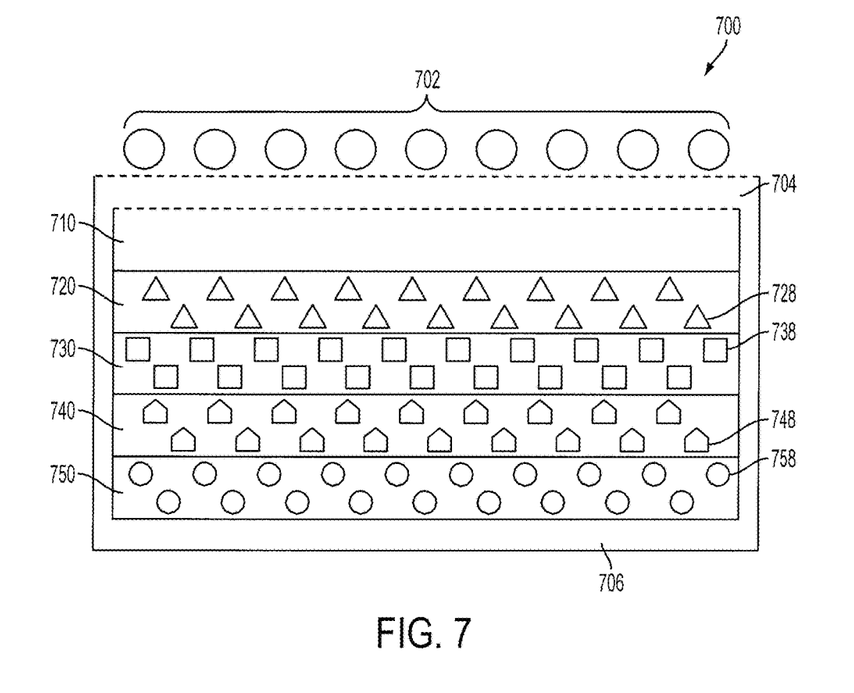
FIG. 7 depicts a multiple phase change system for produce preservation and preparation.

Example 2: A Multiple Phase Change System for Produce Preservation and Preparation A multiple phase change system will be used to protect and condition produce for sale. FIG. 7 shows an illustration of the multiple phase change system 700. The system 700 will have five layers of individually functionalized phase change materials 710, 720, 730, 740, 750. The first layer 710 will be a mixture of methyl oleate (70 weight %) and methyl palmitate (30 weight %) with a melting point of 15° C. The second layer 720 will be a mixture of methyl oleate (60 weight %) and methyl palmitate (40 weight %) with a melting point of 19° C. The second layer 720 will have encapsulated antibacterial gas 728. The third layer 730 will be a mixture of ethyl palmitate (80 weight %) and ethyl stearate (20 weight %) with a melting point of 21° C. The third layer 730 will have encapsulated ripening gas 738 to promote the ripening of fruit or vegetables. The fourth layer 740 will be ethyl palmitate with a melting point of 23° C. The fourth layer 740 will have encapsulated moisture-control compounds 748. The fifth layer 750 will be a mixture of methyl palmitate (80 weight %) and ethyl palmitate (20 weight %) with a melting point of 25° C. The fifth layer 750 will have two encapsulated chemical reactants 758 which, after being released, will react with each other to cause an endothermic reaction. The encapsulated chemical reactants 758 may be acetic acid and sodium bicarbonate. A semipermeable membrane 704 will cover the top of the first layer 710 and the sides of the system and the bottom of the fifth layer 750 will be encased by a packaging material 706 made of polyethylene. The semipermeable membrane 704 will permit the release of the gaseous chemical reactants 728, 738, 748, 758, but will not permit the release of any of the liquid form of the phase change materials 710, 720, 730, 740, 750.

The system 700 will be placed in the bottom of a tray of fruit or vegetables, such as apples 702. The apples 702 will be kept in a refrigerated warehouse storage (temperature of less than or equal to 15° C.) for one week, the refrigeration system in the warehouse will prevent the phase change materials 710, 720, 730, 740, 750 from melting. The tray of apples 702 will be removed from storage and placed at a room temperature of 21° C. As the temperature of the system 700 and the apples 702 gradually rises, the first layer 710 will begin to melt at 15° C., and expose the phase change material of the second layer 720. As the temperature reaches 19° C., the phase change material of the second layer 720 will melt, causing the release of the encapsulated antibacterial gas 728. As the temperature continues to rise, the third phase change material 730 will melt and release the encapsulated ripening gas 738. The ripening gas 738 will permeate upwards to bathe the apples 702 in an atmosphere of ripening gas 738. With continued release in temperature towards room temperature, the fourth phase change material 740 will melt and release the encapsulated moisture-control compounds 748. The moisture-control compounds 748 will absorb moisture within the packaging. Finally, when room temperature is reached, the fifth phase change material 750 will melt and release the encapsulated chemical reactants 758. The chemical reactants 758 will react with each other to cause an endothermic reaction to absorb heat and quell any prior reactions, while maintaining a safe temperature for the apples 702.

Example 3: A Bath Bead Composition

Figure 8:
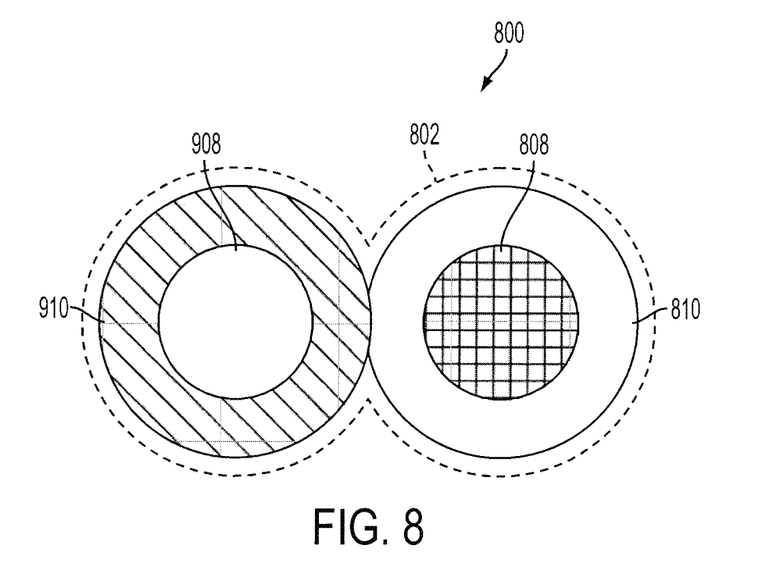
FIG. 8 depicts a cross-section of a bath bead using a phase change system.

A bath bead will be made with two phase change materials encapsulating two different chemical reactants. FIG. 8 depicts a cross-section of such a bath bead 800. A sugar coating 802 will be provided to encase the bead 800. The coating 802 will be a thin, impermeable coating 802 covering the system. The first phase change material 810 will be separate from, but adjacent to a second phase change material 910 in a separate adjacent compartment. The first phase change material 810 will be a mixture of methyl stearate (20 weight %) and ethyl stearate (80 weight %) with a melting point of 34° C. The second phase change material 910 will be ethyl stearate with a melting point of 33° C. Both phase change materials 810, 910 will be blended with rose oil. The first phase change material 810 will have an encapsulated chemical reactant 808 which produces carbon dioxide after it is released and mixed with the water from the bath. The second phase change material 910 will have an encapsulated soap 908 and the soap 908 will release into the water after the second phase change material 910 is melted. The release of the encapsulated soap 908 places soap 908 and fragrant rose oil into the bath water, while the release of the carbon dioxide producing reactant 808 will facilitate mixing and the formation of soap bubbles in the bath water. The bead containing the soap may be separate from or, as shown in FIG. 8, connected to the bead containing the carbon dioxide producing reactant.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of making a phase change system, the method comprising:
    providing a plurality of phase change materials;
    solidifying each of the plurality of phase change materials into a geometrical shape;
    encapsulating at least one chemical reactant in each of the solidified plurality of phase change materials; and
    stacking each of the solidified plurality of phase change materials into layers,
    wherein at least one of the plurality of phase change materials is configured to change from a solid phase to a liquid phase at or above at least one phase transition temperature of the plurality of phase change materials to release the at least one chemical reactant into the liquid phase of the plurality of phase change materials.

2. The method of claim 1, wherein the encapsulating comprises:
    injecting the at least one chemical reactant in a liquid form into each of the solidified plurality of phase change materials.

3. The method of claim 1, further comprising applying a coating over at least a portion of the solidified plurality of phase change materials and the at least one chemical reactant.

4. The method of claim 1, wherein encapsulating the at least one chemical reactant comprises encapsulating at least two chemical reactants capable of reacting with each other when contacted.

5. The method of claim 1, wherein encapsulating the at least one chemical reactant comprises encapsulating a plurality of microcapsules.

6. The method of claim 1, wherein encapsulating at least one chemical reactant comprises encapsulating a liquid, a liquid dispersed in capsules, a gas, a gas dispersed in capsules, a solid, a solid dispersed in capsules, or a combination thereof.

7. The method of claim 1, further comprising configuring the phase change system to trigger at least one event.

8. The method of claim 1, wherein the at least one phase transition temperature is reached when a temperature of an environment surrounding the system is the at least one phase transition temperature, at least one target material reacts with the chemical reactant, or any combination thereof.

* * * * *